(12) United States Patent
Fleischer

(10) Patent No.: US 6,273,873 B1
(45) Date of Patent: *Aug. 14, 2001

(54) FIXATION DEVICE FOR FIXATING A CATHETER RELATIVE TO A SKIN SURFACE PART OF A PERSON

(75) Inventor: Philip Fleischer, Copenhagen (DK)

(73) Assignee: Maersk Medical A/S, Copenhagen (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,804
(22) PCT Filed: Sep. 24, 1997
(86) PCT No.: PCT/DK97/00404
§ 371 Date: Oct. 4, 1999
§ 102(e) Date: Oct. 4, 1999
(87) PCT Pub. No.: WO98/15312
PCT Pub. Date: Jun. 16, 1998

(30) Foreign Application Priority Data

Oct. 4, 1996 (DK) .................................................. DK1093

(51) Int. Cl.[7] ....................................................... A61M 5/32
(52) U.S. Cl. .......................... 604/174; 604/177; 604/180; 604/1
(58) Field of Search ..................................... 604/174, 177, 604/179, 180, 128, DIG. 6, DIG. 26, 905

(56) References Cited

U.S. PATENT DOCUMENTS 4,177,812 * 12/1979 Brown et al. ......................... 604/390
4,419,094   12/1983 Patel ....................................... 604/93

(List continued on next page.)

FOREIGN PATENT DOCUMENTS 2115290   9/1983 (GB) ............................ A61M/31/00
91/07204  5/1991 (WO) ............................ A61M/25/02

(List continued on next page.)

* cited by examiner

*Primary Examiner*—Richard K. Seidel
*Assistant Examiner*—Kevin C. Sirmons
(74) *Attorney, Agent, or Firm*—Klein & Szekeres LLP (57) ABSTRACT

A fixation device for fixating a catheter relative to a skin surface part of a person which catheter defines an outer diameter and is introduced into the interior of the person through the skin surface part substantially perpendicularly relative thereto through a perforation site. The fixation device comprises a pad element to be arranged adjacent to the perforation site and defining a convex marginal surface having a radius of curvature of at least one order of magnitude larger than the outer diameter of the catheter. The marginal surface provides a support surface in relation to the catheter positioned in facial contact therewith for arranging the catheter in a loop and turning the catheter from an orientation substantially perpendicularly relative to the skin surface part to an orientation substantially parallelly with the skin surface part and for preventing the catheter from sliding along the marginal surface. The fixation device further comprises a cover foil of a foil material having opposite first and second surfaces and defining a first end, an adhesive material applied to the first surface of the cover foil, and a connecting foil being connected to the cover foil at the first end thereof and constituting an extension thereof. The pad element is connected to and supported by the connecting foil, which defines a transition area between the supporting element and the cover foil. A folding line is defined within the transition area and the cover foil is foldable onto the pad element along the folding line for arranging the first surface of the cover foil facing towards the pad element for adhering to the skin surface part, for fixating the catheter relative to the pad element and for covering the perforation site.

30 Claims, 5 Drawing Sheets

U.S. PATENT DOCUMENTS

| | | | |
|---|---|---|---|
| 4,645,492 | * 2/1987 | Weeks | 604/174 |
| 4,669,458 | * 6/1987 | Abraham et al. | 128/846 |
| 4,792,480 | * 12/1988 | Freund et al. | 442/378 |
| 5,048,512 | * 9/1991 | Turner et al. | 128/876 |
| 5,282,791 | 2/1994 | Lipton et al. | 604/180 |
| 5,370,627 | 12/1994 | Conway | 604/180 |
| 5,372,589 | 12/1994 | Davis | 604/180 |
| 5,685,859 | * 11/1997 | Kornerup | 604/180 |
| 5,817,044 | * 10/1998 | Evers et al. | 604/20 |
| 5,858,005 | * 1/1999 | Kriesel | 604/180 |

FOREIGN PATENT DOCUMENTS

| | | | |
|---|---|---|---|
| 91/11738 | 6/1993 | (WO) | A61M/5/32 |
| 93/25264 | 12/1993 | (WO) | A61M/25/02 |
| 95/33508 | 12/1995 | (WO) | A61M/25/02 |
| 98/15312 | 4/1998 | (WO) | A61M/25/02 |

FIXATION DEVICE FOR FIXATING A CATHETER RELATIVE TO A SKIN SURFACE PART OF A PERSON

BACKGROUND OF THE INVENTION

The present invention relates to a device for fixating an epidural catheter or a similar drainage catheter to a skin surface part of a patient or person.

The present invention generally relates to the technique of applying and fixating a catheter, such as an epidural catheter, relative to a skin surface part of a patient or person, and more precisely a device for fixating such a catheter relative to a skin surface part of a patient or person.

It is a well-known technique to enter a catheter through the skin of a patient or person, e.g. after a surgical operation.

In certain applications, tiny catheters are to be used which have to be applied to e.g. the back of the person or patient. The size of the catheter itself makes the catheter extremely susceptible to blockings in case the catheter is not properly mounted and in case the patient or person lies on the catheter. The small size of the catheter, e.g. of an epidural catheter also renders it highly likely that the catheter is withdrawn from its intentional position as the patient or person shifts his or her position sitting or lying in the bed or is moved to and from a bed, a chair or moves around as the catheter is very easily caught by the patient or person or caught by a person helping the patient or person.

Furthermore, the technique of applying and fixating a catheter, in particular an epidural catheter, is a complex and time-consuming operation which requires skill and which further often turns out to be inadequate and inappropriate as the epidural catheter is easily pulled out and removed from its intentional position.

Various devices for fixating a catheter have recently been developed as disclosed in eg. GB patent No. 2,115,290, U.S. pat. No. 4,419,094, U.S. pat. No. 4,645,492, U.S. pat. No. 5,282,791, U.S. pat. No. 5,370,627, U.S. pat. No. 5,372,589, WO 91/07204, WO 91/17738, WO 95/33508, WO 93/25264 and WO 93/17738. Reference is made to the above patents and patent applications, and the above U.S. patents are hereby incorporated in the present specification by reference.

The above-mentioned U.S. Pat. No. 5,372,589 discloses a transparent self-adhesive film dressing with a special aerating fenestra, which substantially covers and secures an intravenous catheter to the skin of the patient, for visual inspection, without encouraging growth of bacteria. Although the above-mentioned film dressing is advantageous from the point of view of its extremely simple construction, it can only be used in connection with catheters for percutaneous intubations, which catheters are introduced practically tangentially to the patient's skin, and not in connection with catheters which are introduced perpendicularly to the patient's skin, such as epidural catheters. Application of the self-adhesive film dressing according to U.S. Pat. No. 5,372,589 in connection with an epidural catheter would cause the epidural catheter to bend brusquely at the exit from the puncture point, provoking thus a constriction of the catheter flow channel and impeding an uninterrupted epidural collection and would not prevent the epidural catheter from being pulled out from the position.

The above mentioned published international patent application, publication No. WO 93/25264 discloses a device for fixating a drainage tube, and a drainage tube assembly introduced perpendicularly to the patient's skin, which device comprises a support component including a flange part and a tubular part which are integrally connected through a conical part. The tubular part has a through-going passage for receiving the drainage tube, and the flange part has a surface part to be arranged in surface contact with the skin surface part of the patient. The device also comprises a locking component for locking the drainage tube relative to the tubular part of the support component. The particular assembly of the flange part, the conical part and the tubular part eliminates the risk that the drainage tube may bend at the entrance of the patient's skin and the risk of creation of kinks in the drainage tube. However, the device according to publication No. WO 93/25264 has appreciable dimensions in all three coordinates, making it uncomfortable for the patient if he/she will make a move and squeeze the tube assembly between his/her skin and the bed, at the same time provoking also the interruption of flow in the tube or even the breaking thereof.

Consequently, none of the existing types of fixation devices have been found to meet the requirement of being able to ensure a reliable fixation of a catheter, in particular an epidural catheter, inserted substantially perpendicularly relative to the patient's skin.

SUMMARY OF THE INVENTION

An object of the present invention is to provide a device for fixating an epidural catheter or similar catheter, which device eliminates the risk that the catheter may bend abruptly at the perforation site in the patient's skin or create kinks, and further prevent the catheter from being pulled out in case the catheter is unintentionally squeezed, pressed or in any other way removed from a resting position.

A particular advantage of the device according to the present invention resides in that a single unitary structure is provided which renders it possible, in a single and easily performable operation, to accomplish a secure fixation of the epidural catheter and also make the catheter and the catheter flow less sensitive to the patient's moves or to external pull, squeeze, press or jerk factors.

A particular feature of the device according to the present invention is the provision of a pad which by its curved shape ensures that the epidural catheter by bending over said pad and following the outer contour thereof will form a loop with the same large radius of curvature as the above-mentioned pad, and by its thickness and softness ensures that the epidural catheter will not bend abruptly when exiting the puncture point in the patient's skin.

A further particular feature of the device according to the present invention lies in that the device according to the present invention constitutes a disposable unitary structure which has been presterilized and is applied in a simple manner as a plaster structure to the patient's skin.

The above object, the above advantage and the above features together with numerous other objects, advantages and features which will be evident from the description below are obtained by means of a device for fixating an epidural catheter to the skin surface part of a patient, comprising in accordance with the present invention:

a pad element to be arranged adjacent to the perforation site and defining a convex marginal surface having a radius of curvature of at least one order of magnitude larger than the outer diameter of the catheter, the marginal surface providing a support surface in relation to the catheter positioned in facial contact therewith for arranging the catheter in a loop and turning the catheter from an orientation substantially perpendicularly relative to the skin surface part to an orientation substantially parallelly with the skin surface part and for preventing the catheter from sliding along the marginal surface, a cover foil of a foil material having opposite first and second surfaces and defining a first end, an adhesive material applied to the first surface of the cover foil, and a connecting foil being connected to the cover foil at the first end thereof and constituting an extension thereof, the pad element being connected to and supported by the connecting foil, the connecting foil defining a transition area between the supporting element and the cover foil, a folding line being defined within the transition area, the cover foil being foldable onto the pad element along the folding line for arranging the first surface of the cover foil facing towards the pad element for adhering to the skin surface part, for fixating the catheter relative to the pad element and for covering the perforation site.

The pad element of the fixation device according to the present invention constitutes an element which serves the dual purpose of turning the catheter from an orientation substantially perpendicularly relative to the skin surface part to an orientation substantially parallelly with the skin surface part and supporting the catheter in a loop preventing the catheter from sliding along the marginal surface defined by the pad element and consequently preventing the catheter from being pulled out or otherwise removed from its intentional position extending through the skin of the person through the perforation site.

The fixation device according to the present invention basically comprises three main components viz. the pad element characteristic of the present invention and serving the above described dual purpose, the cover foil and the connecting foil. The cover foil and the connecting foil may according to alternative embodiments of the fixation device according to the present invention be constituted by separate components as the connecting foil may be constituted by a separate foil component or alternatively, the cover foil and the connecting foil may be constituted by a unitary structure as the connecting foil is integral with the cover foil and may be constituted by a single foil or sheet element.

The terms foil and sheet are in the present context to be considered synonymous and are to be considered generic expressions or terms defining a geometric element which has opposite surfaces of fairly large dimensions as compared to the overall thickness of the element in question. The terms foil and sheet are by no means to be construed limited to specific materials and interpretations in relation to e.g. plastic materials, however are to be understood covering plastic foils or sheets and equivalent elements serving the same purpose as plastic foils or sheets.

The adhesion of the cover sheet to the skin surface part of the person in question may be established through configurating the pad element and the cover foil so as to allow the cover foil to cover the pad element and at the same time adhere to the skin surface part. According to the presently preferred embodiment of the fixation device according to the present invention, the pad element defines a pad area and the first surface of the cover foil defines an area substantially exceeding the pad area. Consequently, in accordance with the above described preferred embodiment of the fixation device according to the present invention, the cover sheet readily adheres to the skin surface part of the person in question as the cover sheet is applied covering the pad element. It is to be understood that the cover sheet preferably includes a complete adhesive covering at its first surface allowing the cover sheet to adhere in facial contact to the pad element and also adhere to the skin surface part of the person in question.

The connecting foil may in accordance with a first embodiment of the device according to the present invention be provided with an adhesive covering at a surface thereof coextensive with the surface of the cover foil serving the purpose of adhering to the adhesive of the cover foil as the cover foil is folded onto the connecting foil. Additionally or alternatively, the connecting foil is preferably provided with an adhesive covering at a surface thereof opposite to the first surface of the cover foil and consequently serving the purpose of causing the connecting foil to adhere to the skin surface part of the patient or person prior to the folding of the cover onto the pad element and the connecting foil and at least temporarily fixating the device according to the present invention in its intentional position at the perforation site.

The adhesive covering of the connecting foil at the surface thereof coextensive with the surface of the cover foil also serves the purpose of at least temporarily fixating the catheter relative to the connecting foil as the catheter is arranged in the above described loop and in contact with the adhesive covering of the connecting foil.

For further improving the fixation of the catheter relative to the skin surface part of the patient or person, the connecting foil according to the above described preferred embodiment of the device according to the present invention preferably has an extension serving the purpose of covering and adhering to the catheter.

Dependent on the configuration of the pad element characteristic of the present invention and also the provision of an adhesive covering at a surface of the connecting foil coextensive with the surface of the cover foil, the pad element may be provided with an adhesive covering at the convex marginal surface for causing the catheter in the above described loop to adhere to the pad element. Additionally or alternatively, the pad element may be provided with an adhesive surface covering for adhering to the cover foil as the cover foil is folded onto the pad element.

The device according to the present invention preferably comprises an extension of the connecting foil for covering and adhering to the catheter for improving the fixation of the catheter relative to the skin surface part. Furthermore or alternatively, the connecting foil may be provided with a fixation support adjacent the pad element for attaching the catheter to the skin surface part of the patient or person.

For improving the main purpose of preventing that the catheter is bent abruptly or blocked, the pad element may be provided with one or more notches for receiving and fixating the catheter relative to the pad element and consequently supporting and properly securing the catheter relative to the pad element.

In order to allow visual inspection of the perforation site and also allow visual inspection of the arrangement of the catheter relative to the device according to the present invention and consequently relative to the perforation site, the cover foil may advantageously be provided with a transparent area allowing visual inspection of the perforation site.

In order to render it possible to handle the fixation device before applying it to the catheter and to the skin surface part of the person, to which skin surface part the catheter is to be fixated, the device according to the present invention preferably further comprises release foils covering all the adhesive areas. The release foils may be constituted by a siliconized paper, siliconized or non-siliconized polyester, polypropylene, polyethylene or a similar plastic material.

The cover foil of the fixating device according to the present invention may be configurated in an arbitrary shape provided the cover foil fulfils the above requirement of fixating the catheter and the catheter-supporting connecting foil relative to the skin surface part. Thus, according to alternative geometrical embodiments of the fixation device according to the present invention, the cover foil may be of a rectangular configuration, a quadratic configuration, a circular configuration, an elliptic configuration or a combination of the above configurations.

For preventing the ingress of bacteria into the perforation site, the foil covering the perforation site is preferably made from a material providing a bacteria barrier. Provided the cover foil as discussed above is provided with a transparent area, the transparent area is advantageously and preferably covered by a gas and liquid impermeable and bacteria barrier defining transparent foil. Alternatively, provided the cover foil is provided without a transparent area, the cover foil or at least a part of the cover foil covering the perforation site is preferably constituted by a material providing a bacteria barrier.

The sheet material of the cover foil of the fixation device according to the present invention may be made from any appropriate material which may be used as a cover foil material. Provided the adhesive layers are substantially water-impermeable, the sheet material may be made from water-impermeable or water-permeable material. In order to hinder any penetration of water through the cover foil from the environment into the area covered by the bandage, the sheet material is, however, preferably a substantially water-impermeable material such as spun bond, spun lace, woven or non-woven foil materials of polyester, nylon, polypropylene, polyethylene, polyurethane, polyvinylchloride, clear tape or other transparent or non-transparent material, or combinations thereof.

The pads may be made of any appropriate soft material such as a fibrous synthetic or natural material, e.g. cotton, viscose, rayon or the like, synthetic or natural rubber or foamed plastic foils such as a polyester foam, a polyurethane foam, EVA foam (Ethylene Vinyl Acetate foam).

The individual components of the fixation device according to the present invention including the cover foil, the adhesive covering, the connecting foil and also any additional adhesives and/or release foils etc. may readily be chosen by a person having ordinary skill in the art from materials which are well-known in the art for medical application including medical grade supporting element materials, cover foils, release foils, adhesives etc.

The adhesive layer may be constituted by a medical grade acrylic adhesive, a medical, natural or synthetic rubber resin adhesive or other medical grade adhesive.

BRIEF DESCRIPTION OF THE DRAWINGS

The invention will now be further described with reference to the drawings, in which.

DETAILED DESCRIPTION OF THE INVENTION

In the following examples, parts and elements of different embodiments of an epidural catheter fixation device having the same function are designated the same reference numeral but primed a number of times, the priming number being one unit less than the number of the embodiment. For example, an element 20 in the first embodiment will be designated the reference numeral 20' in the second embodiment, 20" in the third, etc.

In the following examples and in the claims terms like "lower side" and "upper side" used in connection with the sides of the respective foils will be construed as meaning "skin-facing side" and "opposite the skin-facing side", respectively.

Figure 1A:
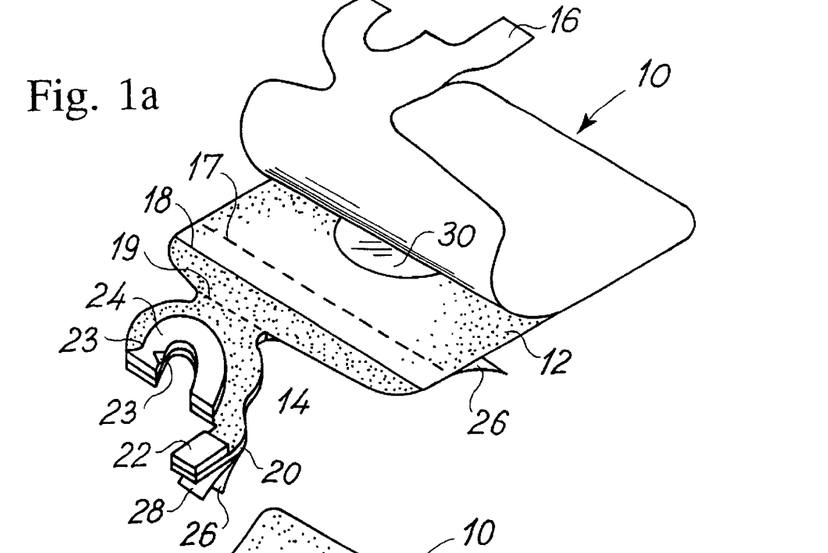
FIG. 1a is a schematic and perspective view of a first embodiment of an epidural catheter fixation device according to the present invention.

In FIG. 1a a first embodiment of an epidural catheter fixation device is designated the reference numeral 10 in its entirety. The epidural catheter fixation device comprises an oblong, substantially rectangular cover foil 12 having a first adhesive side and a second non-adhesive side. Centrally the cover foil 12 is provided with an inspection window 30 which is made by removing the respective portion of the cover foil providing an aperture within the cover foil 12 which is covered by a transparent plastic foil. A double adhesive connecting foil 14 is further provided defining a broad base having the same width as the cover foil 12 and is adhesively attached with the broad base to the non-adhesive side of the cover foil 12 in extension thereto, the broad base narrowing and then evading and forming a U-shaped foil portion with outwardly pointing uneven branches.

On the one side of the double adhesive connecting foil 14, corresponding to the non-adhesive side of the cover foil 12, a first, U-shaped pad 20 with uneven branches is attached, the pad having the same shape as the evased, U-shaped foil portion of the double adhesive connecting foil 14. A substantially U-shaped pad or second pad 24 with substantially even branches is adhered to the opposite side of the double adhesive connecting foil 14, corresponding to the adhesive side of the cover foil 12. The substantially U-shaped pad 24 defines an outer convex marginal surface constituting a support and contact surface against which a catheter to be fixated by means of the device 10 is positioned as will be described in greater details below. A third pad 22 is adhered to the double adhesive connecting foil 14 at the extremity of the longer branch of the double adhesive connecting foil 14 on the same side thereof as the pad 24. A first release foil 16 covers the adhesive side of the cover foil 12 and a first adhesive side of the double adhesive connecting foil 14. A second release foil 26 covers the opposite side of the double adhesive connecting foil 14 and also covers an adhesive applied to the lower side of the pad 20, and a third release foil 28 covers the portion of the second adhesive side of the double adhesive connecting foil 14 corresponding to the length of the pad 22. A continuous line 18 defines the margin of the cover foil 12, a dashed line 17 defines the margin of the broad base of the double adhesive connecting foil 14, and a dashed line 19 defines the margin of the pad 20.

Figures 1B, 1C:
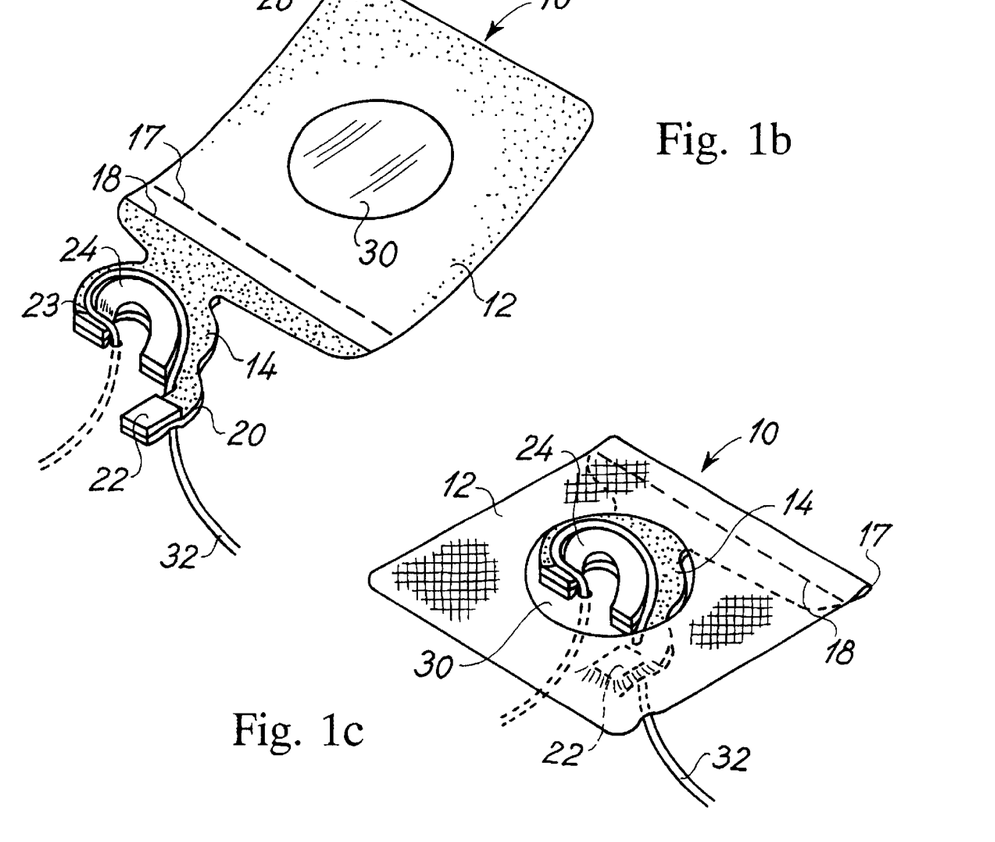
FIG. 1b is a schematic and perspective view of the embodiment of the epidural catheter fixation device of FIG. 1a, illustrating a first step of applying the epidural catheter fixation device for fixating an epidural catheter relative to a skin surface part of a person or patient.
FIG. 1c is a schematic and perspective view illustrating the epidural catheter of FIG. 1b finally fixated by means of the epidural catheter fixation device.

FIG. 1b shows the first embodiment 10 of an epidural catheter fixation device of FIG. 1a in a first step of applying the fixation device onto a skin surface part of a person for fixating an epidural catheter 32 relative to the skin surface part. Initially, the second release foil 26 shown in FIG. 1a is removed exposing the lower side of the double adhesive connecting foil 14 and also the adhesive applied to the lower side of the pad 20. The fixation device 10 is then positioned adjacent to the perforation site as the U-shaped pad 24 is positioned juxtaposed the perforation site allowing the epidural catheter 32 to be bent backwardly and supported in recesses 23 also shown in FIG. 1a provided in the U-shaped pad 24. The epidural catheter 32 perforates the skin perpendicularly to the patient's skin surface part through a perforation site 34 and is bent backwardly relative to the pad 24 and wrapped around the rounded portion of the pad 24 and positioned in contact with the outer convex marginal surface of the pad 24. The epidural catheter 32 is then positioned below the third pad 22 and below the longer extremity of the U-shaped pad 20 which is connected to the third pad 22 through the corresponding longer branch of the double adhesive connecting foil 14. The epidural catheter 32 is then fixated relative to the skin surface part of the person as the adhesive applied to the lower side of the pad 20 is caused to adhere to the skin surface and also to the epidural catheter 32. The wrapping of the catheter 32 around the U-shaped pad 24 firstly ensures that the catheter 32 does not bend brusquely, in an acute angle, which might lead to catheter constriction and preventing the flow of fluid through the catheter. The wrapping of the catheter around the pad 24, secondly forms a loop in a plane substantially perpendicular to the plane of the catheter perforating the skin surface at the perforation site and pull relief in case the catheter 32 is pulled, squeezed, pressed, jerked or in any other way removed from its resting position on the connecting sheet 14, thereby diminishing the discomfort caused to the patient and the risk that the catheter may be extracted unwillingly from its insertion site.

Thereupon, the first release foil 16 shown in FIG. 1a is removed as is illustrated in FIG. 1b and the cover foil 12 is bent or folded onto the connecting foil 14 and also onto the pad 24 supporting the epidural catheter 32 in the above described non-bending and pull relieving manner as the cover foil 12 is bent along the dashed line 17 constituting the margin of the broad base of the support foil 14. As the cover foil 12 is folded onto the pad 24, the perforation site is also sealed as is illustrated in FIG. 1c disclosing the final positioning of the fixation device 10 relative to the skin surface part of the person. As the cover foil 12 is folded onto the pad 24 and also onto the skin surface part of the person, the adhesive of the lower side of the cover foil 12 adheres to the skin surface part and also adheres to the epidural catheter 32. In the above described first embodiment, the inspection window 30 allows visual inspection of the perforation site and also inspection of the position of the epidural catheter supported by the device. It is to be realized that the epidural catheter is in its bent wrapped around the pad 24 adhered to the upper adhesive of the double adhesive connecting foil 14. Provided the inspection window 30 is not provided, the epidural catheter is sandwiched between the cover foil 12 and adhere to the adhesive of the lower side thereof and the upper adhesive side of the double adhesive connecting foil 14. The sandwiching of the epidural catheter in the bent and wrapped around position relative to the pad 24 further improves the fixation of the epidural catheter relative to the skin surface part of the person.

Figure 2:
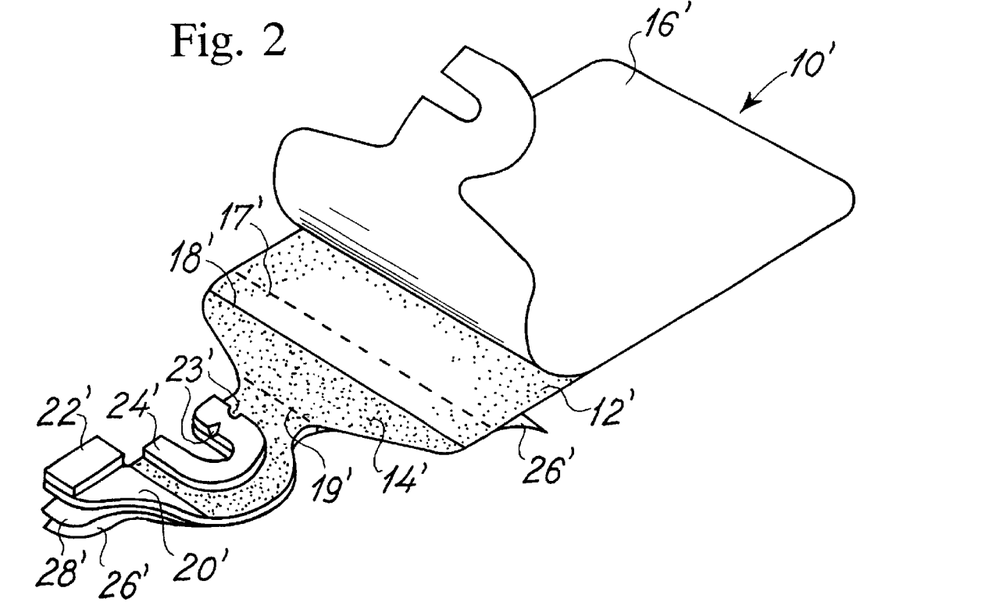
FIG. 2 is a schematic and perspective view similar to the view of FIG. 1a of a second embodiment of the epidural catheter fixation device according to the present invention.

FIG. 2 shows a second embodiment of an epidural catheter fixation device 10' according to the present invention, which embodiment is designated the reference numeral 10' in its entirety and is very similar in construction to the first embodiment 10 presented in FIG. 1a, but differing in the position and shape of the U-shaped extension of the connecting foil 14'. The succession of layers in this second embodiment of the catheter fixation device 10' is the same as in the first embodiment, i.e. the first release foil 16', the U-shaped pad 24' with substantially even branches, one of the branches being provided with two opposite grooves 23', the pad 22' coplanar with the pad 24', the double adhesive connecting foil 14', the U-shaped pad 20', the second release foil 26', and the third, intermediate release foil 26' between the second release foil 26 and the end of the longer branch of the U-shaped pad 20'. However, the second embodiment 10' differs from the first embodiment 10 in that the U-shaped pad 20' is shifted 90° relative to the overall orientation of the double adhesive connecting foil 14' and the cover foil 12' as compared to the orientation of the pad 24 in relation to the double adhesive connecting foil 14 and the cover foil 12 of the first embodiment 10. Thus, as is evident from FIG. 1c, the cover foil 12 is applied in an orientation substantially transversly relative to the orientation of the epidural catheter 32, the cover foil 12' is applied lengthwise or longitudinally relative to the overall orientation of the epidural catheter which is to be fixated by means of the device 10'.

Figure 3:
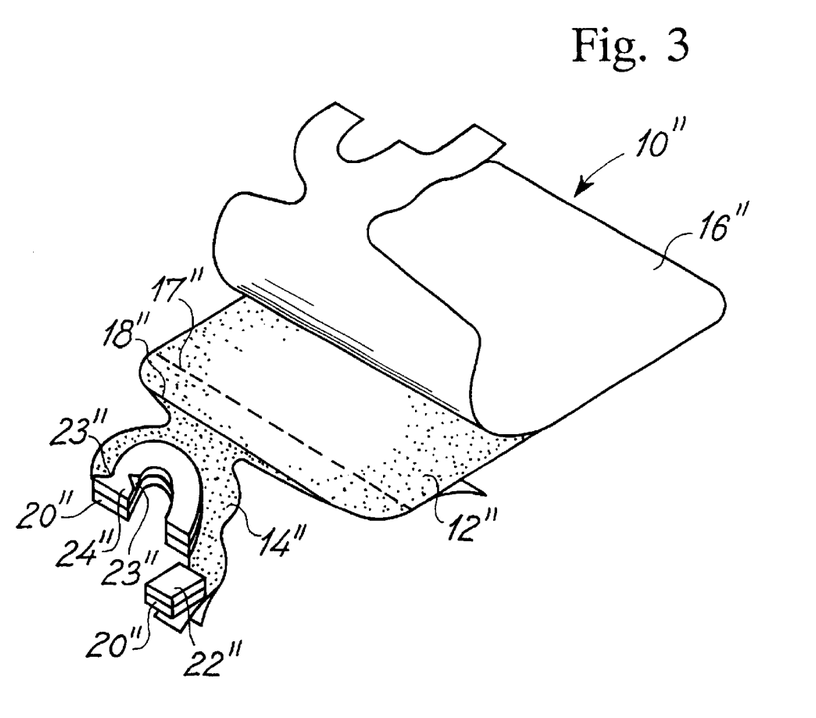
FIG. 3 is a schematic and perspective view similar to the view of FIG. 1a of a third embodiment of the epidural catheter fixation device according to the present invention.

FIG. 3 shows a third embodiment of the epidural catheter fixation device 10" according to the present invention, which embodiment is identical in shape to the first embodiment 10 presented in FIG. 1a, but its construction is simplified in the respect that this third embodiment does not employ the above-mentioned pad 20, providing a simpler construction. The succession of layers in the U-shaped assembly of layers is: the first release foil 16", the U-shaped pad 24" with substantially even branches, one of the branches being provided with two opposite grooves 23", the pad 22" coplanar with the pad 24", the double adhesive connecting foil 14", the second release foil 26", and the third, intermediate release foil 28" between the second release foil 26" and the end of the longer branch of the double adhesive connecting foil 14". Any of the above-mentioned embodiments in the FIGS. 2, and 3, which are not explicitly provided with a inspection window, may be provided with such a window, and its shape may vary, being, for example, substantially rectangular, oval, elliptic, etc.

Figure 4A:
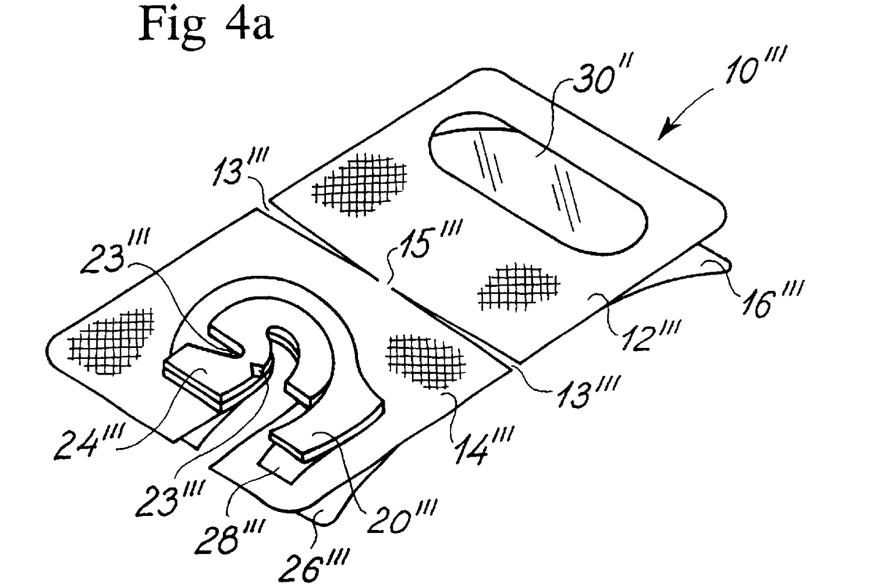
FIG. 4a is a schematic and perspective view similar to the view of FIG. 1a of a fourth embodiment of the epidural catheter fixation device according to the present invention.
Figure 4B:
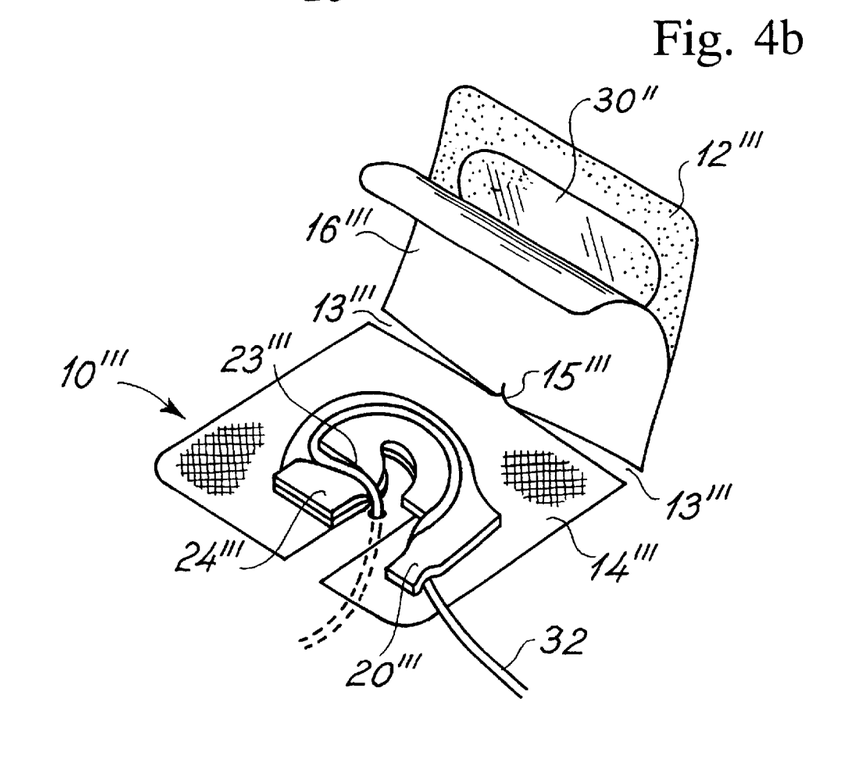
FIG. 4b is a schematic and perspective view similar to the view of FIG. 1b of the fourth embodiment of the epidural catheter fixation device.

FIG. 4a is a schematic and perspective view of a fourth embodiment 10'" of the epidural catheter fixation device according to the present invention, which epidural catheter fixation device 10'" comprises the following succession of layers: the first release foil 16'", the cover foil 12'" provided with two symmetrical transversal cuts in the median region thereof, dividing the cover foil 12''' into a proximal part and a distal part, and an oblong cutout provided longitudinally from the proximal end towards the median region of the cover foil 12''', the adhesive layer provided between the release foil 16''' and the cover foil 12''', the first pad 20''' adhesively adhered to the distal end of the cutout and following its contours on approximately half the penetration depth of the cutout into the proximal part of the cover foil 12''', and the second pad 24''' adhesively adhered to the first pad 20''' and following the contours of the cutout but on a more reduced length of the cutout periphery than the first pad 20'''. Between one end of the first pad 20''' and the cover foil 12''', a cover foil 28''' is provided, and the cover foil 12''' is at the distal end thereof provided with a viewing window 32''' which in the FIGS. 4a and 4b has the shape of an oblong rectangle with rounded ends, but which may have any other suitable above-mentioned form, such as circular, oval, elliptic, etc. The fourth embodiment 10''' of the epidural catheter fixation device according to the present invention is applied in a manner which is different from the above-mentioned embodiments, as in the fourth embodiment there is only one adhesive layer continuously provided upon the catheter-supporting, skin-attaching proximal part of the catheter fixating device 10''' and the catheter-covering distal part of the same catheter fixating device 10'''. Consequently, as seen in FIG. 4b, the provision of the two symmetrical, transversal cuts in the median region of the cover foil 12''' renders it possible to rotate the distal part of the cover foil 12''' 180° so that the adhesive side of the distal part may be superposed the non-adhesive part of the cover foil 12''' supporting the first and the second pad 20''' and 24''', respectively, and the catheter 32.

Figure 5A:
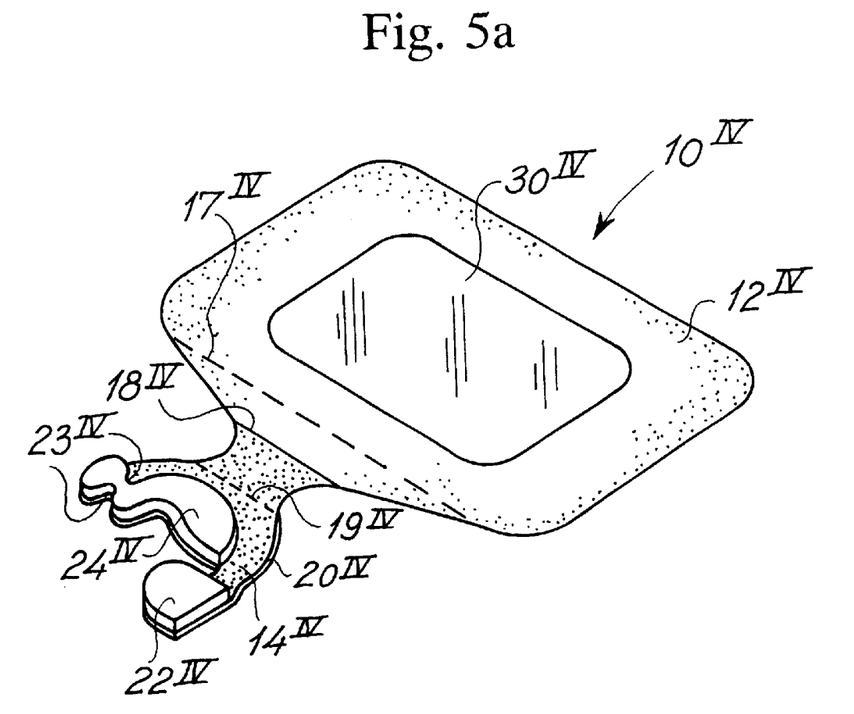
FIG. 5a is a schematic and perspective view similar to the view of FIG. 1a of a fifth embodiment of the epidural catheter fixation device according to the present invention.
Figure 5B:
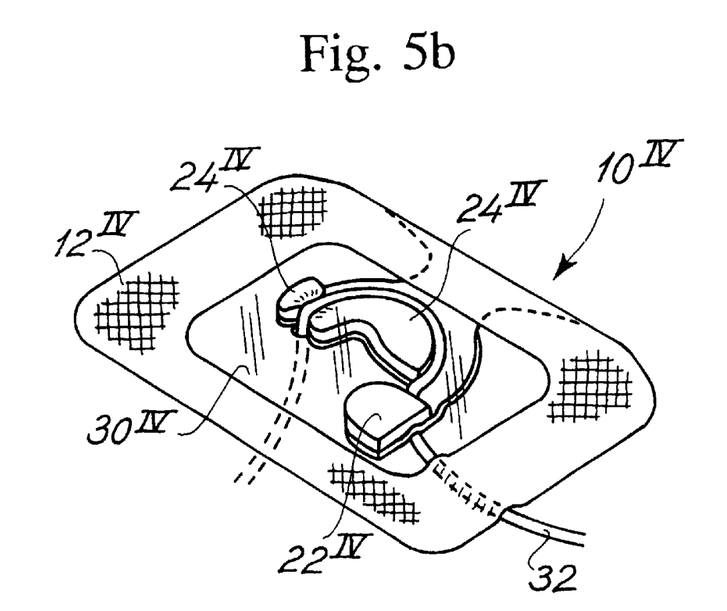
FIG. 5b is a schematic and perspective view similar to the view of FIG. 1c of the fifth embodiment of the epidural catheter fixation device.

FIGS. 5a and 5b are schematic and perspective views of a fifth and preferred embodiment $10^{iv}$ of the epidural catheter fixation device $10^{iv}$ according to the present invention. The succession of layers in this fifth embodiment of the present invention is the same as in the first embodiment of the invention, i.e. the first pad $20^{iv}$, the connecting foil $14^{iv}$ having a broad bottom, continuing with a narrowing and evading into a lobe, the cover foil $12^{iv}$ partially overlapping the broader lobe of the connecting foil $14^{iv}$ and provided with the inspection window $30^{iv}$, and the second and a third pad $24^{iv}$ and $22^{iv}$, respectively attached to the extremity of the lobe, the second pad $24^{iv}$ being provided with two grooves $23^{iv}$ for placing the epidural catheter 32. The configuration of the fifth and preferred embodiment is optimized as to limit the requirements of dexterity from the user's part and also the multiple bending of the epidural catheter 32, thus reducing the risk of constriction of the flow. The epidural catheter 32 is thus placed above the section between the two grooves $23^{iv}$, then wrapped around the semicircular curvature of the pad $24^{iv}$, and finally introduced under the pad $22^{iv}$ which adheres to the patients skin, thus ensuring a first step in fixating the epidural catheter 32 to the patient's skin. A second step comprises the fixation of the entire assembly comprising the epidural catheter 32 and the lobe-shaped part of the connecting foil $14^{iv}$ supported on the first pad $20^{iv}$ and supporting the second and the third pad $24^{iv}$ and $22^{iv}$, respectively, by folding the cover foil $12^{iv}$ over the assembly along the folding line $17^{iv}$ which marks the transition from a two-layer thickness of the fixation device $10^{iv}$ to a single layer. The third pad $22^{iv}$ has the main function of providing temporary stable support for the epidural catheter $32^{iv}$ after it is wrapped around the semicircular portion of the second pad $24^{iv}$ and before it is introduced under the first pad $20^{iv}$. The finally fixated epidural catheter $10^{iv}$ is seen in FIG. 5b.

Figure 6:
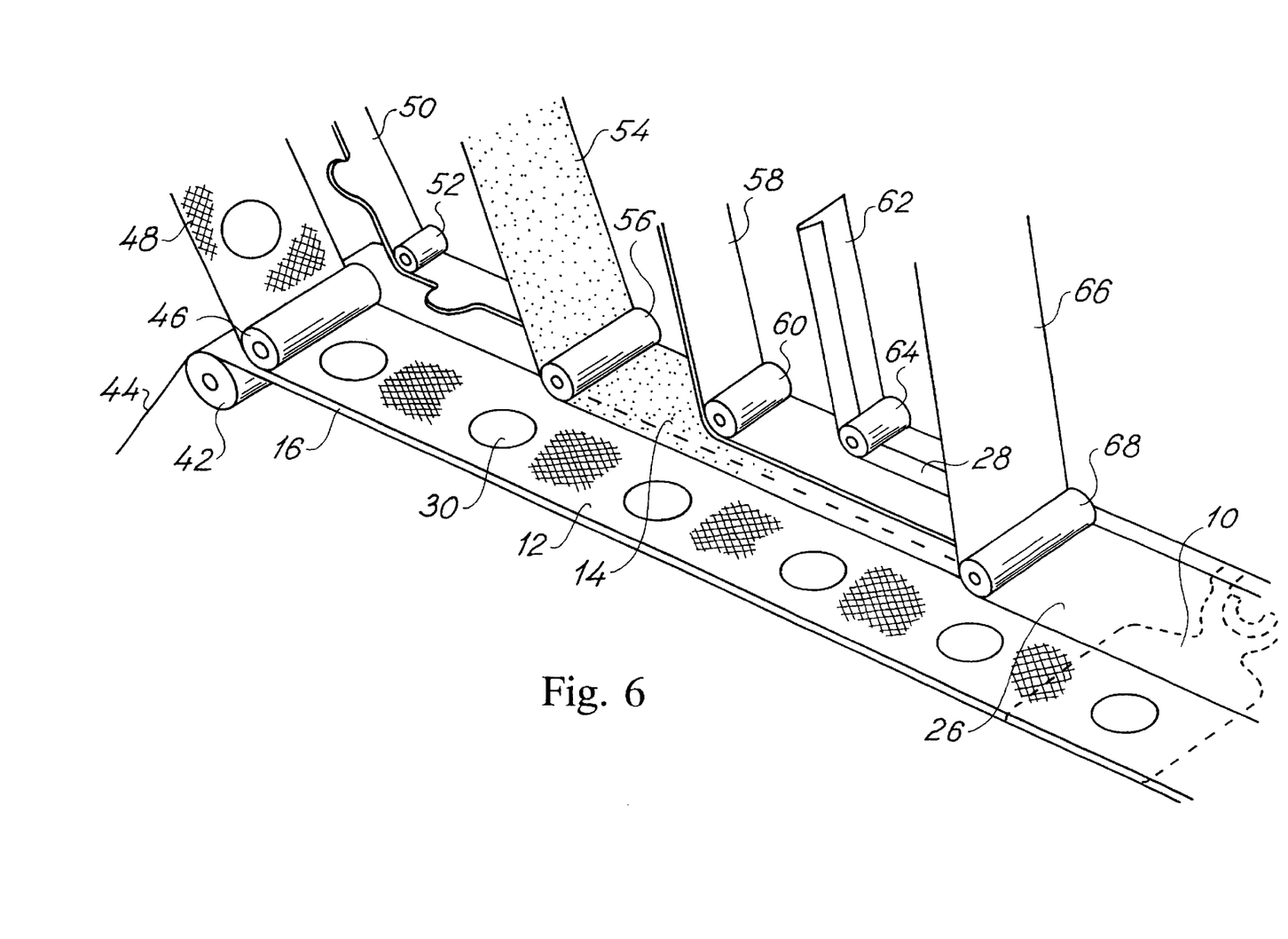
FIG. 6 is a schematic and perspective view of a preferred method of producing the first embodiment of an epidural catheter fixation device according to the present invention shown in FIGS. 1a, 1b, 1c and illustrating the multilayer structure of the epidural catheter fixation device.

FIG. 6 is a schematic and perspective view of a preferred method of producing the first embodiment 10 of an epidural catheter fixation device according to the present invention shown in FIGs. 1a, 1b, 1c and illustrating the multilayer structure of the epidural catheter fixation device. According to the method illustrated in FIG. 6 a system of rollers feed and attach to each other by superposition a series of layers of material. A roller 42 feeds release foil 44, a roller 46 feeds a cover foil 48 which contains an adhesive layer on its lower side, a roller 52 feeds a pad sheet 50 that after stamping generates the pads 22 and 24, a roller 56 feeds a double adhesive sheet 54 which overlaps a cover foil 48 partially, a roller 60 feeds a pad sheet 58 which adheres to a connecting foil 54, a roller 64 feeds a release foil 62 which covers the pad sheet 58, and a roller 68 feeds a release foil 66 which covers the release foil 62, the pad sheet 58, the connecting foil 54, and a portion of the non-adhesive side of the cover foil 48. The resulting multilayer structure is thereafter fed through a stamping machine which shapes the multilayer material into the desired profile.

EXAMPLE

The epidural catheter fixation device shown in FIGS. 5a and 5b was made from the following materials: The cover foil $12^{iv}$ was made from a non-woven polyamide sheet of approx. 45 g/m². The overall length of the cover foil $12^{iv}$ was 120 mm and the overall width of the maximum lateral dimension was 98 mm. The transparent film which is part of the two-layered cover foil $12^{iv}$ and covers the inspection window $30^{iv}$ was a semi-permeable polyurethane sheet. The adhesive material applied to the cover foil $12^{iv}$ was a medical grade acrylic adhesive. The pads $20^{iv}$, $22^{iv}$ and $24^{iv}$ were made of polyethylene foam. The connecting foil $14^{iv}$ was a polyethylene foil coated on both sides with a medical grade acrylic adhesive. The adhesives of the fixating device were covered by a siliconized release paper.

Although the present invention has been described above with reference to specific, presently preferred embodiments of the fixation device according to the present invention, the present invention is, however, by no means to be construed as limited to the above embodiments, as numerous modifications, combinations and amendments are readily perceivable by a person having ordinary skill in the art, within the scope of the present invention as defined in the appended claims.

What is claimed is:

1. A fixation device for fixating a catheter relative to a skin surface part of a person, said catheter defining an outer diameter and being introduced into the interior of said person through said skin surface part substantially perpendicularly relative thereto through a perforation site, comprising:

a pad element having a major surface to be arranged in parallel relationship with said skin surface part in a position adjacent to said perforation site and further having an outwardly curved convex marginal surface extending transversely relative to said major surface and having a radius of curvature of at least one order of magnitude larger than said outer diameter of said catheter, said marginal surface providing a support surface in relation to said catheter positioned in facial contact therewith for arranging said catheter in a loop that lies in a plane that is substantially parallel to the major surface of the pad, and turning said catheter from an orientation substantially perpendicular relative to said skin surface part to an orientation substantially parallel with said skin surface part and for preventing said catheter from sliding along said marginal surface, a cover foil of a foil material having opposite first and second surfaces and defining a first end, an adhesive material applied to said first surface of said cover foil, and a connecting foil being connected to said cover foil at said first end thereof and constituting an extension thereof, said pad element being connected to and supported by said connecting foil, said connecting foil defining a transition area between said supporting element and said cover foil, a folding line being defined within said transition area, said cover foil being foldable onto said pad element along said folding line for arranging said first surface of said cover foil facing towards said pad element for adhering to said skin surface part, for fixating said catheter relative to said pad element and for covering said perforation site.

2. The device according to claim 1, wherein said connecting foil is integral with said cover foil.

3. The device according to any of the claim 1, said pad element defining a pad area, and said first surface of said cover foil defining an area substantially exceeding said pad area.

4. The device according to any of the claim 1, said connecting foil being provided with an adhesive covering at a surface thereof coextensive with said surface of said cover foil.

5. The device according to any of the claim 4, said connecting foil being provided with an adhesive covering at a surface thereof opposite to said first surface of said cover foil.

6. The device according to claim 5, said connecting foil having a longer branch for covering and adhering to said catheter.

7. The device according to any of the claim 1, said pad element being provided with an adhesive covering at said convex marginal surface.

8. The device according to any of the claim 1, said pad element being provided with an adhesive surface covering.

9. The device according to any of the claim 1, said connecting foil providing a fixation support adjacent said pad element for attaching said catheter to said skin surface part of said person.

10. The device according to any of the claim 1, said pad element having two opposed notches.

11. The device according to any of the claim 1, said cover foil having a transparent area allowing visual inspection of said perforation site.

12. The device according to any of the claim 1, said cover foil being covered by a release foil covering said adhesive material of said first surface of said cover foil.

13. The device according to claim 1, said cover foil being of a configuration selected from the group consisting of a rectangular configuration, a quadrilateral configuration, a circular configuration, an elliptical configuration.

14. The device according to any of the claim 1, said cover foil being made of a water-permeable material.

15. The device according to claim 1, said cover foil being made of a water-impermeable material.

16. A catheter fixation system for use at a perforation site on the skin surface of a person, the system comprising:

a catheter having an outer diameter dimensioned for introduction through the skin surface at the perforation site; and a device for fixating the catheter relative to the skin surface, the device comprising:

a pad element having a major surface to be arranged in parallel relationship with said skin surface in a position adjacent to said perforation site and further having an outwardly curved convex marginal surface extending transversely relative to said major surface and having a radius of curvature of at least one order of magnitude larger than said outer diameter of said catheter, said marginal surface providing a support surface in relation to said catheter positioned in facial contact therewith for (a) arranging said catheter in a loop that lies in a plane that is substantially parallel to the major surface of the pad, (b) turning said catheter from an orientation substantially perpendicular relative to said skin surface to an orientation substantially parallel with said skin surface, and (c) preventing said catheter from sliding along said marginal surface;

a cover foil of a foil material having opposite first and second surfaces and defining a first end; an adhesive material on said first surface of said cover foil; and a connecting foil connected to said cover foil at said first end thereof and constituting an extension thereof, said pad element being connected to and supported by said connecting foil, said connecting foil defining a transition area located between said supporting element and said cover foil and defining a folding line, wherein said cover foil is foldable onto said pad element along said folding line so that said first surface of said cover foil faces toward said pad element for adhering to said skin surface;

whereby said catheter is fixated relative to said pad element while said perforation site is covered.

17. The device according to claim 16, wherein said connecting foil is integral with said cover foil.

18. The device according to claim 16, said pad element defining a pad area, and said first surface of said cover foil defining an area substantially exceeding said pad area.

19. The device according to claim 16, said connecting foil being provided with an adhesive covering at a surface thereof coextensive with said surface of said cover foil.

20. The device according to claim 16, said connecting foil provided with an adhesive covering at a surface thereof opposite to said first surface of said cover foil.

21. The device according to claim 20, said connecting foil having an extension for covering and adhering to said catheter.

22. The device according to claim 16, said pad element being provided with an adhesive covering at said convex marginal surface.

23. The device according to claim 16, said pad element being provided with an adhesive surface covering.

24. The device according to claim 16, said connecting foil providing a fixation support adjacent said pad element for attaching said catheter to said skin surface.

25. The device according to claim 16, said pad element having two opposed notches.

26. The device according to claim 16, said cover foil having a transparent area allowing visual inspection of said perforation site.

27. The device according to claim 16, said cover foil being covered by a release foil covering said adhesive material of said first surface of said cover foil.

28. The device according to claim 16, said cover foil being of a configuration selected from the group consisting of a rectangular configuration, a quadrilateral configuration, a circular configuration, an elliptical configuration.

29. The device according to claim 16, said cover foil being made of a water-permeable material.

30. The device according to claim 16, said cover foil being made of a water-impermeable material.

* * * * *